United States Patent
DeLuca et al.

(10) Patent No.: US 9,814,736 B2
(45) Date of Patent: *Nov. 14, 2017

(54) USE OF 2-METHYLENE-19-NOR-(20S)-1α,25-DIHYDROXYVITAMIN $D_3$ AND CALCIMIMETICS TO TREAT SECONDARY HYPERPARATHYROIDISM

(71) Applicant: Wisconsin Alumni Research Foundation, Madison, WI (US)

(72) Inventors: Hector F. DeLuca, Deerfield, WI (US); Lori A. Plum, Arena, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/338,924

(22) Filed: Oct. 31, 2016

(65) Prior Publication Data

US 2017/0042913 A1 Feb. 16, 2017

Related U.S. Application Data

(63) Continuation of application No. 14/710,746, filed on May 13, 2015, now Pat. No. 9,539,264.
(Continued)

(51) Int. Cl.
*A61K 31/59* (2006.01)
*A61K 31/593* (2006.01)
(Continued)

(52) U.S. Cl.
CPC .......... *A61K 31/593* (2013.01); *A61K 9/0053* (2013.01); *A61K 31/137* (2013.01); *A61K 45/06* (2013.01)

(58) Field of Classification Search
CPC .............................. A61K 31/593; A61K 45/06
(Continued)

(56) References Cited

U.S. PATENT DOCUMENTS 5,843,928 A 12/1998 DeLuca et al.
6,136,799 A 10/2000 Li et al.
(Continued)

FOREIGN PATENT DOCUMENTS

JP 2002543115 12/2002
JP 2003528833 9/2003
(Continued)

OTHER PUBLICATIONS

Khan et al., "NPrimary hyperparathyroidism: pathophysiology and impact on bone," CMAJ 2000;163(2):184-7.
(Continued)

*Primary Examiner* — T. Victor Oh
(74) *Attorney, Agent, or Firm* — Andrus Intellectual Property Law, LLP

(57) ABSTRACT

Disclosed are methods of administering 2-methylene-19-nor-(20S)-1α,25-dihydroxyvitamin $D_3$ to treat and/or prevent secondary hyperparathyroidism and/or its accompanying symptoms in a subject having or at risk for developing secondary hyperparathyroidism, including a subject previously administered a calcimimetic.

21 Claims, 10 Drawing Sheets

Related U.S. Application Data

(60) Provisional application No. 62/098,112, filed on Dec. 30, 2014.

(51) Int. Cl.
  *A61K 45/06* (2006.01)
  *A61K 31/137* (2006.01)
  *A61K 9/00* (2006.01)

(58) Field of Classification Search
  USPC .......................................................... 514/167
  See application file for complete search history.

(56) References Cited

U.S. PATENT DOCUMENTS

| | | | |
|---|---|---|---|
| 7,563,783 B2 | 7/2009 | DeLuca et al. | |
| 9,034,853 B2* | 5/2015 | DeLuca | A61K 31/593 514/167 |
| 9,205,096 B2* | 12/2015 | DeLuca | A61K 31/593 |
| 9,539,264 B2* | 1/2017 | DeLuca | A61K 31/593 |
| 2002/0028830 A1 | 3/2002 | DeLuca et al. | |
| 2005/0124591 A1 | 6/2005 | Tian et al. | |
| 2005/0187201 A1 | 8/2005 | DeLuca et al. | |
| 2006/0003973 A1 | 1/2006 | DeLuca et al. | |
| 2006/0135492 A1 | 6/2006 | DeLuca et al. | |
| 2006/0171983 A1 | 8/2006 | Tian et al. | |
| 2006/0276534 A1 | 12/2006 | Martin et al. | |
| 2010/0087404 A1 | 4/2010 | Mazess et al. | |
| 2011/0034426 A1 | 2/2011 | DeLuca et al. | |
| 2013/0295083 A1 | 11/2013 | DeLuca et al. | |
| 2014/0005152 A1 | 1/2014 | DeLuca et al. | |
| 2014/0187522 A1 | 7/2014 | DeLuca et al. | |
| 2014/0315809 A1 | 10/2014 | Walter et al. | |

FOREIGN PATENT DOCUMENTS

| | | |
|---|---|---|
| JP | 2007508298 | 4/2007 |
| JP | 2007523162 | 8/2007 |
| WO | 0066098 | 11/2000 |
| WO | 0172292 | 10/2001 |
| WO | 0205823 | 1/2002 |
| WO | 2005039592 | 5/2005 |
| WO | 2005082456 | 9/2005 |
| WO | 2009/026265 A1 | 2/2009 |
| WO | 2011119610 | 9/2011 |

OTHER PUBLICATIONS

Vanhooke et al., "New analogs of 2-methylene-19-nor-(20S)-1,25-dihydroxyvitamin D3 with conformationally restricted side chains: evaluation of biological activity and structural determination of VDR-bound conformations," Arch Biochem Biophys, Apr. 15, 2007, 460(2):161-165.

Yamamoto et al, "2-Methylene-19-nor-(20S)-1alpha,25-dihydroxyvitamin D3 Potently Stimulates Gene-specific DNA Binding of the Vitamin D Receptor in Osteoblasts", Journal of Biological Chemistry, 2003, 278(34): 31756-31765.

Zella et al., "2MD, a Potent and Selective 1,25-Dihydroxyvitamin D Analog, Suppresses PTH in 5/6-Nephrectomized Rats and in Post-menopausal Women", American Journal of Nephrology, Mar. 6, 2014, pp. 1-50.

Advisory Action for U.S. Appl. No. 12/845,173 dated Aug. 28, 2014.

Advisory Action for U.S. Appl. No. 12/845,173 dated Oct. 21, 2013.

Barycki et al., "Removal of the 20-methyl group from 2-methylene-19-nor-(20S)-1alpha,25-dihydroxyvitamin D(3) (2MD) selectively eliminates bone calcium mobilization activity," Bioorg Med Chem., Nov. 15, 2009, 17 (22):7658-69.

Bradford, Marion M., "A Rapid and Sensitive Method for the Quantitation of Microgram Quantities of Protein Utilizing the Principle of Protein-Dye Binding", Analytical Biochemistry, 1976, 72: 248-254.

Brown et al., "The Noncalcemic Analogue of Vitamin D, 22-Oxacalcitriol, Suppresses Parathyroid Hormone Synthesis and Secretion", J. Clin. Invest., 1989, 84: 728-732.

Chen et al, "Modulatory Effects of 1,25-Dihydroxyvitamin D3 on Human B Cell Differentiation", The Journal of Immunology, 2007, 179: 1634-1647.

Curriculum Vitae for Hector F. DeLuca.

Darwish et al., "Identification of a Transcription Factor That Binds to the Promoter Region of the Human Parathyroid Hormone Gene", Archives of Biochemistry and Biophysics, 1999, 365(1): 123-130.

Declaration for U.S. Appl. No. 12/845,173 dated Sep. 27, 2013.

DeLuca, "The development of a bone- and parathyroid-specific analog of vitamin D: 2-methylene-19-Nor-(20S)-1alpha,25-dihydroxyvitamin D3," Bonekey Rep, Mar. 5, 2014, 2:514.

DeLuca et al., "The vitamin D analogue 2MD increases bone turnover but not BMD in postmenopausal women with osteopenia: results of a 1-year phase 2 double-blind, placebo-controlled, randomized clinical trial," J Bone Miner Res., Mar. 2011, 26(3):538-545.

DeLuca et al., "Vitamin D: The Vitamin and the Hormone", Fed. Proc., 1974, 33: 2211-2219.

DeLuca H.F. "Therapeutic potential of the 2-aklyl and 2-alkylidene-19-nor-(20S)-odified analogs of 1-25-dihydroxyvitamin D3." Journal of Steroid Biochemistry & Molecular Biology 89-90 (2004) 67-73.

Delmez, et al., "Hyperphosphatemia: Its Consequences and Treatment in Patients with Chronic Renal Disease", American Journal of Kidney Diseases, 1992, XIX(4): 303-317.

Demay et al., "Sequences in the Human Parathyroid Hormone Gene that Bind the 1,25-Dihydroxyvitamin D3 Receptor and Mediate Transcriptional Repression in Response to 1,25-Dihydroxyvitamin D3", Proc. Natl. Acad. Sci. USA, 1992, 89: 8097-8101.

Final Office Action for U.S. Appl. No. 12/845,173 dated Jul. 3, 2011.

Final Office Action for U.S. Appl. No. 12/845,173 dated Mar. 31, 2014.

International Preliminary Report on Patentability for PCT/US2010/043551 dated Feb. 16, 2012.

International Search Report and Written Opinion, PCT International Application No. PCT/US2013/031574, dated Apr. 25, 2013.

International Search Report and Written Opinion in PCT/US2010/043551, filed Jul. 28, 2010.

Ke et al., "A New Vitamin D Analog, 2MD, Restores Trabecular and Cortical Bone Mass and Strength in Ovariectomized Rats With Established Osteopenia", Journal of None and Mineral Research, 2005, 20: 1742-1755.

Kim, James, "Effects of 1α,25-dihydroxyvitamin D3 on the MRL/MpJ-fas/lpr Model of Systemic Lupus Erythematosus", Ph.D. Thesis, University of Wisconsin-Madison, 2009.

Komaba et al. "Diseases of the parathyroid gland in chronic kidney disease". Clin Exp Nephrol (2011) 15:797-809.

Lopez-Hilker, et al., "Phosphorus Restriction Reverses Hyperparathyriodism in Uremia Independent of Changes in Calcium and Calcitriol", American Journal of Physiology—Renal Physiology, 1990, 259: 432-437.

Meyrier et al., "The Influence of High Calcium Carbonate Intake on Bone Disease in Patients Undergoing Hemodialysis", Kidney International, 1973, 4: 146-153.

Moriniere, et al., "Subtitution of Aluminium Hydroxide by High Doses of Calcium Carbonate in Patients on Chronic Haemodialysis: Disappearance of Hyperaluminaemia and Equal Control of Hyperparathyriodism", Proc. EDTA, 1982, 19: 784-787.

National Kidney Foundation, Inc. Part 4. Definition and Classification of Stages of Kidney Disease, American Journal of Kidney Diseases, vol. 39, No. 2, Suppl 1. Feb. 2002, pp. S46-S75.

Office Action for U.S. Appl. No. 12/845,173 dated Aug. 24, 2012.

Office Action for JP2012-523654 dated Aug. 29, 2014.

Office Action for U.S. Appl. No. 12/845,173 dated Nov. 6, 2014.

Portale, et al., "Effect of Dietary Phosphorus on Circulating Concentrations of 1,25-Dihydroxyvitamin D and Immunoreactive Parathyroid Hormone in Children with Moderate Renal Insufficiency", J. Clin. Invest., 1984, 73: 1580-1589.

(56) References Cited

OTHER PUBLICATIONS

Quarles, et al., "Prospective Trial of Pulse Oral Intravenous Calcitriol Treatment of Hyperparathyriodism in ESRD", Kidney International, 1994, 45: 1710-1721.
Response for U.S. Appl. No. 12/845,173 dated Apr. 6, 2015.
Response for U.S. Appl. No. 12/845,173 dated Jul. 25, 2014.
Response for U.S. Appl. No. 12/845,173 dated Nov. 4, 2011.
Response for U.S. Appl. No. 12/845,173 dated Oct. 2, 2013.
Response for U.S. Appl. No. 12/845,173 dated Jan. 23, 2013.
Sato et al., "New 19-nor-(20S)-1alpha,25-dihydroxyvitaimin D3 analogs strongly stimulate osteoclast formation both in vivo and in vitro," Bone, Feb. 2007, 40(2):293-304.
Sato et al, "New 19-nor-(20S)-1alpha,25-dihydroxyvitamin D3 analogs strongly stimulate osteoclast formation both in vivo and in vitro", Bon, 2007, 40: 293-304.
Search Report for SG11201408731W dated Jun. 23, 2015.
Shevde et al., "A potent analog of 1alpha,25-dihydroxyvitamin D3 selectively induces bone formation", PNAS, 2002, 99 (21): 13487-13491.
Sibilska et al., "1-desoxy analog of 2MD: synthesis and biological activity of (20S)-25-hydroxy-2-methylene-19-norvitamin D3," J Steroid Biochem Mol Bio, Jul. 2010, 121(1-2):51-55.
Slatopolsky et al., "New analog of calcitriol, 19-nor-1,25-(OH)2D2, suppresses parathyroid hormone secretion in uremic rats in the absence of hypercalcemia," American Journal of Kidney Diseases, Nov. 1995, 26(5):852-860.
Slatopolsky et al., "Marked Suppression of Secondary Hyperparathyroidism by Intravenous Administration of 1,25-Dihydroxycholecalciferol in Uremic Patients", J. Clin. Invest., 1984, 74: 2136-2143.
Slatopolsky et al., "Calcium Carbonate as a PHosphate Binder in Patients with Chronic Renal Failure Undergoing Dialysis", New Engl. J. Med., 1986, 315: 157-161.
U.S. Appl. No. 09/616,164, filed Jul. 14, 2000.
Written Opinion for SG11201408731W dated Aug. 14, 2015.

Brown et al., "The Noncalcemic Analogue of Vitamin D, 22-Oxacalcitriol, Suppresses Parathyroid Hormone Synthesis and Secretion", Journal of Clinical Investigation, 84:728-732, 1989.
Brown et al., "Selective Vitamin D Analogs and their Therapeutic Applications" (1994).
Darwish and DeLuca "Identification of a transcription factor that binds to the promoter region of the human parathyroid hormone gene" (1999).
DeLuca, "Vitamin D: The vitamin and the hormone" (1974).
DeLuca, "Vitamin D: Recent advances" (1983).
Demay et al., "Sequences in the human parathyroid hormone gene that bind the 1,25-dihydroxyvitamin D3 receptor and mediate transcriptional repression in response to 1,25-dihydroxyvitamin D3",Proc. Natl. Acad. Sci. usa, 89:8097-8101, 1992.
James Wonkee Kim, "Effects of calcitriol on the MRL/MpJ-fas/lpr model of systemic lupus erythematosus" (2009).
Shevde et al., "A potent analog of 1alpha,25-dihydroxyvitamin D3 selectively induces bone formation", PNAS, 99 (21):13487-13491, Oct. 15, 2002.
Slatopolsky et al., "Marked Suppression of Secondary Hyperparathyroidism by Intravenous Administration of 1,25-Dihydroxycholecalciferol in Uremic Patients", Journal of Clinical Investigation, 74:2136-2143, 1984.
"Part 4. Definition and Classification of Stages of Chronic Kidney Disease," American Journal of Kidney Diseases, Feb. 2002, 39(2): Suppl. 1: S46-S75.
DeLuca et al., "2MD, A New Treatment for Secondary Hyperparathyroidism: A Phase 2B, Double-Blind, Randomized, Placebo-Controlled Study in Hemodialysis Patients," Nov. 15, 2014.
Abstract for DeLuca et al., "2-Methylene-19-nor-(20S)-1a,25-Dihydroxyvitamin D3, a Promising New Therapeutic for Secondary Hyperparathyroidism," Minceral Disease: Vitamin D, PTH, and FGF-23-II, Nov. 14, 2014.
International Search Report and Written Opinion for PCT/US2015/065175 dated Feb. 23, 2016.

* cited by examiner

Figure 2

| Parameter | Statistic | Cohort 1 110 ng (N = 6) | Cohort 2 220 ng (N = 6) | Cohort 3 330 ng (N = 5) | Cohort 4 440 ng (N = 8) | Cohort 5 550 ng (N = 6) |
|---|---|---|---|---|---|---|
| Corr Ser Ca Change: Baseline to Week 4 (mg/dL) | Mean (SD) | -0.8 (1.0) | 0.0 (0.4) | 0.5 (0.5) | 0.2 (0.2) | 0.5 (0.8) |
| Ser P Change: Baseline to Week 4 (mg/dL) | Mean (SD) | 1.0 (0.9) | -0.1 (0.6) | -0.2 (1.1) | 0.4 (1.1) | -0.4 (2.6) |
| 2 consecutive iPTH < 150 pg/mL | n (%) | 0 | 0 | 0 | 0 | 0 |
| 2 consecutive Corr Ser Ca > 10.6 mg/dL | n (%) | 0 | 0 | 0 | 0 | 0 |
| 2 consecutive Ca X P > 62 (mg$^2$/dL$^2$) | n (%) | 0 | 1 (17) | 0 | 0 | 0 |

Figure 5

Demographics and Baseline Characteristics

| Characteristic | Statistic | Placebo (N = 28) | DP001 (N = 34) |
|---|---|---|---|
| Age (yr) | Mean (SD) | 60 (8) | 58 (15) |
| Gender: Male | n (%) | 14 (50) | 17 (50) |
| Race: White | n (%) | 13 (46) | 17 (50) |
| Race: Black | n (%) | 11 (39) | 15 (44) |
| Race: Asian | n (%) | 2 (7) | 1 (3) |
| Race: Native Am. | n (%) | 2 (7) | 1 (3) |
| BMI (kg/m$^2$) | Mean (SD) | 33 (6) | 34 (8) |
| Prior use of Cinacalcet | n (%) | 9 (32) | 10 (29) |
| Corr Ser Ca (mg/dL) | Mean (SD) | 8.8 (0.6) | 8.9 (0.5) |
| Ser P (mg/dL) | Mean (SD) | 4.5 (1.1) | 4.9 (1.4) |
| Corr Ser Ca X P (mg$^2$/dL$^2$) | Mean (SD) | 39.6 (9.4) | 43.5 (12.4) |
| Serum iPTH (pg/mL) | Mean (SD) | 428 (138) | 547 (316) |

Figure 9

Safety Results – Endpoints

| Safety Endpoints | Statistic | Placebo (N = 28) | DP001 (N = 34) |
|---|---|---|---|
| Patients with 2 consecutive iPTH <150 pg/mL | n (%) | 0 | 14 (41.2) |
| Patients with 2 consecutive Corr Ca ≥11 mg/dL | n (%) | 0 | 0 |
| Patients with 2 consecutive Corr Ca X P >70 mg$^2$/dL$^2$ | n (%) | 0 | 3 (8.8) |

Figure 10

Safety Results – Adverse Events

| | Placebo (N = 28) | DP001 (N = 34) |
|---|---|---|
| Number AEs | 85 | 66 |
| Number of Subjects with at Least 1 AE; n (%) | 20 (71%) | 24 (71%) |
| SAEs* (n) | 4 Subjects 9 SAEs | 6 Subjects 9 SAEs |
| AEs "Possibly" or "Probably" Related to Study Drug (n) | 4 | 4 |

* No SAE was judged by Investigators to be related to study drug

USE OF 2-METHYLENE-19-NOR-(20S)-α,25-DIHYDROXYVITAMIN D₃ AND CALCIMIMETICS TO TREAT SECONDARY HYPERPARATHYROIDISM

CROSS-REFERENCE TO RELATED PATENT APPLICATIONS

The present application is a continuation application of U.S. application Ser. No. 14/710,746, filed on May 13, 2015, and published as U.S. Publication No. 2016/0184328, on Jun. 30, 2016, which application claims the benefit of priority under 35 U.S.C. §119(e) to U.S. Provisional Patent Application No. 62/098,112, filed on Dec. 30, 2014, the contents of which are incorporated herein by reference in their entireties.

BACKGROUND

This invention relates to vitamin D compounds useful in treating and/or preventing secondary hyperparathyroidism and/or the symptoms thereof, and more particularly to the use of the vitamin D compound 2-methylene-19-nor-(20S)-1α,25-dihydroxyvitamin $D_3$, otherwise referred to herein as "2MD," to treat and/or prevent secondary hyperparathyroidism and/or the symptoms thereof in patients having secondary hyperparathyroidism that previously were treated with calcimimetics.

Secondary hyperparathyroidism refers to the excessive secretion of parathyroid hormone (PTH) by the parathyroid glands in response to hypocalcemia (low blood calcium levels). This disorder is especially seen in patients with chronic renal failure and often is abbreviated as "SHPT" in medical literature.

Renal disease has become an increasingly important health problem in virtually every country in the world including highly developed countries such as the United States. Presently there are about 250,000 patients in the United States on renal dialysis who have lost almost complete use of their kidneys. There are approximately ten times more patients who have lost some degree of renal function due to renal disease and are progressing to complete renal failure. Renal failure is evidenced by a decreased glomeruli filtration rate (GFR) from a high value of 110 ml/minute/1.73 $m^2$ to 30 ml/minute/1.73 $m^2$ where dialysis is often initiated, and may be referred to as Stage 5, Chronic Kidney Disease (CKD).

Many factors contribute to the development of renal disease. High blood pressure is one of the significant contributors, as is having Type I or Type II diabetes. Current treatments for renal failure are limited to hemodialysis, an extremely expensive procedure that currently is supported by federal governments because individuals typically cannot afford this procedure on their own. The annual cost of renal disease in the United States alone is over $42 billion. Accordingly, effective methods for preventing renal disease and treating symptoms thereof would not only provide a major health benefit but would also provide a major economic benefit.

Secondary hyperparathyroidism (SHPT) has been successfully managed with the use of two types of agents: active vitamin D analogs (AVDs) alone or with the addition of a calcimimetic (CM). Regarding vitamin D's role in managing SHPT, it is now universally accepted that vitamin D must first be 25-hydroxylated in the liver and subsequently 1α-hydroxylated in the kidney before it can be converted to its active form, namely 1α,25-$(OH)_2D_3$ or "calcitriol." (See DeLuca, "Vitamin D: The vitamin and the hormone," Fed. Proc. 33, 2211-2219, 1974; and DeLuca & Schnoes, "Vitamin D: Recent advances," Ann. Rev. Biochem. 52, 411-439, 1983). Calcitriol then stimulates a number of physiological processes including: stimulating the intestine to absorb calcium, stimulating the kidney to reabsorb calcium, stimulating the intestine to absorb phosphate, and stimulating bone to mobilize calcium when signaled by high parathyroid hormone (PTH) levels. These actions result in a rise in plasma calcium and phosphorus levels that bring about the healing of bone lesions such as rickets and osteomalacia and prevent the neurological disorder of hypocalcemic tetany.

Accordingly, SHPT is a universal complication in patients with chronic renal failure because patients with chronic renal failure are unable to convert 25-hydroxyvitamin $D_3$ from the liver to its active form of 1α,25-$(OH)_2D_3$ via 1α-hydroxylation in the kidney. As a result of low levels of circulating 1α,25-$(OH)_2D_3$ in patients with chronic renal failure, intestinal calcium absorption is minimal which subsequently results in insufficient serum calcium levels. In addition, during chronic renal failure, the failing kidneys do not adequately excrete phosphate. When this happens, insoluble calcium phosphate forms in the body and removes calcium from circulation. Ultimately, low levels of circulating 1α,25-$(OH)_2D_3$ and inadequate phosphate excretion contribute to hypocalcemia and secondary hyperparathyroidism because when the parathyroid glands sense a low level of serum calcium (i.e., hypocalcemia), the parathyroid glands secrete an elevated amount of PTH in order to raise calcium mobilization from bone to raise serum calcium.

In addition to SHPT resulting from renal failure, SHPT also can result from gastrointestinal malabsorption syndromes (e.g., chronic pancreatitis, small bowel disease, and malabsorption-dependent bariatric surgery in which the intestines do not absorb vitamins and minerals properly), where these syndromes are characterized by insufficient absorption of the fat soluble vitamin D resulting in low levels of circulating 1α,25-$(OH)_2D_3$. Other less common causes of secondary hyperparathyroidism are long-term lithium therapy, vitamin D deficiency, malnutrition, vitamin D-resistant rickets, or hypermagnesemia (i.e., abnormally high blood magnesium levels).

As such, overt symptoms of SHPT include increased secretion of PTH. Left unchecked, the elevated secretion of PTH observed in SHPT will lead to the development of renal osteodystrophy. High PTH levels can also lead to: 1) weakening of the bones; 2) calciphylaxis (when calcium forms clumps in the skin and lead to ulcers and potentially death of surrounding tissue); 3) cardiovascular complications; 4) abnormal fat and sugar metabolism; 5) itching (pruritis); and 6) low blood counts (anemia). Less overt symptoms of SHPT include bone and joint pain, bone deformities, broken bones (fractures), swollen joints, kidney stones, increased urination, muscle weakness and pain, nausea, loss of appetite, upper abdominal pain, fatigue, and depression.

Because SHPT results from low levels of circulating calcitriol, calcitriol has been administered as a therapeutic in order to supplement the low levels of circulating calcitriol in patients with SHPT. In the treatment of SHPT, it is well known that calcitriol binds to the vitamin D receptor (VDR) located in the parathyroid glands to suppress both growth and proliferation of the parathyroid cells and expression of the preproparathyoid gene. (See Demay et al., "Sequences in the human parathyroid hormone gene that bind the 1,25-dihydroxyvitamin $D_3$ receptor and mediate transcriptional repression in response to 1,25-hydroxyvitamin $D_3$." Proc. Natl. Acad. Sci. USA 89, 8097-8101, 1992; and Darwish &

DeLuca, "Identification of a transcription factor that binds to the promoter region of the human parathyroid hormone gene," Arch. Biochem. Biophys. 365, 123-130, 1999). Because of its ability to suppress parathyroid hormone (PTH), calcitriol has been used with success in the treatment of secondary hyperparathyroidism. (See Slatopolsky et al., "Marked Suppression of Secondary Hyperparathyroidism by Intravenous Administration of 1,25-dihydroxycholecalciferol in Uremic Patients," J. Clin. Invest. 74:2136-2143, 1984). However, the use of calcitriol in the treatment of SHPT is not without its drawbacks because calcitriol may cause hypercalcemia resulting from calcitriol's potent action on intestinal calcium absorption and bone mineral calcium mobilization.

As such, less calcemic analogs of calcitriol that exhibit diminished activity on intestinal calcium absorption and/or bone mineral calcium mobilization have been developed and have been found to be nearly as effective as calcitriol in suppressing PTH secretion by cultured bovine parathyroid cells. These include 22-oxacalcitriol (OCT), (Brown et al., "The Non-Calcemic Analog of Vitamin D, 22-oxacalcitriol (OCT) Suppresses Parathyroid Hormone Synthesis and Secretion," J. Clin. Invest. 84:728-732, 1989), as well as 1,25-$(OH)_2$-16-ene-23-yne-$D_3$, 1,25-$(OH)_2$-24-dihomo-$D_3$, and 1,25-$(OH)_2$-24-trihomo-22-ene-$D_3$. 22-oxacalcitriol has been examined in detail for this action in vivo. (See Brown et al., "Selective Vitamin D Analogs and their Therapeutic Applications," Sem. Nephrol 14:156-174, 1994, reporting that 22-oxacalcitriol, despite its rapid clearance in vivo, could suppress PTH mRNA). Low, submaximal doses of calcitriol and OCT exhibited comparable inhibition. OCT also has been shown to suppress serum PTH in uremic rats and dogs.

Another analog of calcitriol with low calcemic and phosphatemic action is 19-nor-1,25-$(OH)_2D_2$, which is also known as paricalcitol or 19-nor-1α,25-dihydroxy-ergocalciferol. Paricalcitol injection is available commercially as Zemplar® from Abbott Laboratories, Abbott Park, Ill. A paricalcitol (Zemplar®) injection is described in U.S. Pat. No. 6,136,799 and has been approved by the FDA and is marketed for the prevention and treatment of secondary hyperparathyroidism associated with chronic renal failure (CKD Stage 5 or end-stage renal disease (ESRD), GFR<15 mL/min/1.73 $m^2$).

A newer class of drug used to treat SHPT are the so-called "calcimimetics," one of which is commercially available as Sensipar®(cinacalcet) in the United States and Australia, and as Mimpara® in the European Union. A calcimimetic (CM) is a drug that mimics the action of calcium on the parathyroid gland by allosteric activation of the calcium-sensing receptor that is expressed in the parathyroid gland. In particular, CMs increase the sensitivity of calcium-sensing receptors in the parathyroid gland and trick the parathyroid gland into thinking that there is a sufficient level of serum calcium. As a result of the receptor thinking that there is sufficient serum calcium, PTH secretion is reduced. Calcimimetics have achieved positive responses and are FDA approved for use in patients on dialysis, but have not been approved for use in chronic kidney disease pre-dialysis because, among other concerns, CMs also can increase phosphorus levels. Further, CMs cause hypocalcemia and are provided together with a vitamin D analog (AVD) to both prevent hypocalcemia and to help in suppression of serum PTH. Often CMs are employed when an AVD by itself is unable to suppress the PTH without also causing hypercalcemia. Thus, both a CM and an AVD may be administered to treat SHPT in some patient.

Thus, a drug for treating SHPT that can suppress PTH with minor effects on calcium and phosphate metabolism would be an ideal tool for the control and treatment of secondary hyperparathyroidism. Here, a highly potent active vitamin D analog (AVD), namely, 2-methylene-19-nor-(20S)-1α,25-dihydroxyvitamin $D_3$, referred to herein as "2MD", is shown to suppress PTH production while maintaining serum calcium and serum phosphate in the normal range. (See also U.S. Published Application No. 2014/0005152, the content of which is incorporated herein by reference in its entirety). As such, 2MD may be useful for treating SHPT in patients that previously were treated with other AVDs or calcimimetics (CMs).

SUMMARY

It has now been discovered that the vitamin D analog 2-methylene-19-nor-(20S)-1α,25-dihydroxyvitamin $D_3$ (2MD) has the ability to treat secondary hyperparathyroidism as well as symptoms of secondary hyperparathyroidism when administered under well-controlled conditions to a subject in need thereof, including a subject previously treated with a calcimimetic (CM). It also now been discovered that the vitamin D analog 2MD has the ability to prevent secondary hyperparathyroidism as well as symptoms of secondary hyperparathyroidism when administered under well-controlled conditions to a subject in need thereof, including a subject previously requiring a calcimimetic and an active vitamin D analog (AVD). Thus, 2MD has the unique property among vitamin D compounds to eliminate or reduce the need for a CM in the management of secondary hyperparathyroidism.

In one embodiment, the present invention provides a novel method of treating secondary hyperparathyroidism by administering a therapeutically effective amount of a composition comprising 2-methylene-19-nor-(20S)-1α,25-dihydroxyvitamin $D_3$ (2MD) or pharmaceutically acceptable salts thereof as the active agent to a subject exhibiting symptoms of secondary hyperparathyroidism, including a subject previously treated with a calcimimetic, preferably without inducing hypercalcemia in the subject.

In another embodiment, the present invention provides a novel method of treating symptoms of secondary hyperparathyroidism by administering a therapeutically effective amount of a composition comprising 2-methylene-19-nor-(20S)-1α,25-dihydroxyvitamin $D_3$ (2MD) or pharmaceutically acceptable salts thereof as the active agent to a subject exhibiting symptoms of secondary hyperparathyroidism, including a subject previously treated with a calcimimetic, preferably without inducing hypercalcemia in the subject.

In yet another embodiment, the present invention provides a novel method of preventing secondary hyperparathyroidism by administering a therapeutically effective amount of a composition comprising 2-methylene-19-nor-(20S)-1α,25-dihydroxyvitamin $D_3$ (2MD) or pharmaceutically acceptable salts thereof as the active agent to a subject at risk of developing secondary hyperparathyroidism, including a subject previously treated with a calcimimetic, preferably without inducing hypercalcemia in the subject.

In still another embodiment, the present invention provides a novel method of preventing symptoms of secondary hyperparathyroidism by administering a therapeutically effective amount of a composition comprising 2-methylene-19-nor-(20S)-1α,25-dihydroxyvitamin $D_3$ (2MD) or pharmaceutically acceptable salts thereof as the active agent to a subject at risk of developing secondary hyperparathyroidism, including a subject previously treated with a calcimimetic, preferably without inducing hypercalcemia in the subject.

In the disclosed methods, the 2-methylene-19-nor-(20S)-1α,25-dihydroxyvitamin $D_3$ (2MD) may be formulated in an oral, topical, transdermal, parenteral, injectable or infusable form of a pharmaceutical composition comprising a suitable dose of 2MD. In some embodiments, pharmaceutical compositions may comprise 2MD (or pharmaceutically acceptable salts thereof) in a minimal dose of at least about 0.01, 0.05, 0.1, 0.5, 1.0, 5.0, 10.0, 50.0, 100.0, 500.0 or 1000.0 μg/gm of the composition. In other embodiments, pharmaceutical compositions may comprise 2MD (or pharmaceutically acceptable salts thereof) in a maximal dose no greater than 1000.0, 500.0, 100.0, 50.0, 10.0, 5.0, 1.0, 0.1, or 0.05 μg/gm of the composition. The compositions may comprise 2MD within dose ranges having as end-points any of these disclosed doses (e.g., where 2MD represents 0.01-1000.0 μg/gm of the composition). Minimal and/or maximal doses may be administered at any suitable frequency, such as daily, three times per week, weekly, or other frequencies.

Patients suitable for the disclosed treatment and prevention methods may include a patient having or at risk for developing secondary hyperparathyroidism or the symptoms thereof including a patient previously administered a calcimimetic. For example, patients suitable for the disclosed treatment and prevention methods may include a patient previously administered cinacalcet.

BRIEF DESCRIPTION OF THE FIGURES

FIG. 2. Safety parameter versus concentration of DP001 (2MD) for patients of FIG. 1. Data are presented as mean (standard deviation (SD)).

FIG. 5. Demographic and baseline characteristics of study enrollees.

FIG. 9. Study enrollees exceeding safety threshold values for iPTH, Ca, and P.

FIG. 10. Number of adverse events (AEs) and serious adverse events (SAEs) for study enrollees.

DETAILED DESCRIPTION

Figure 1:
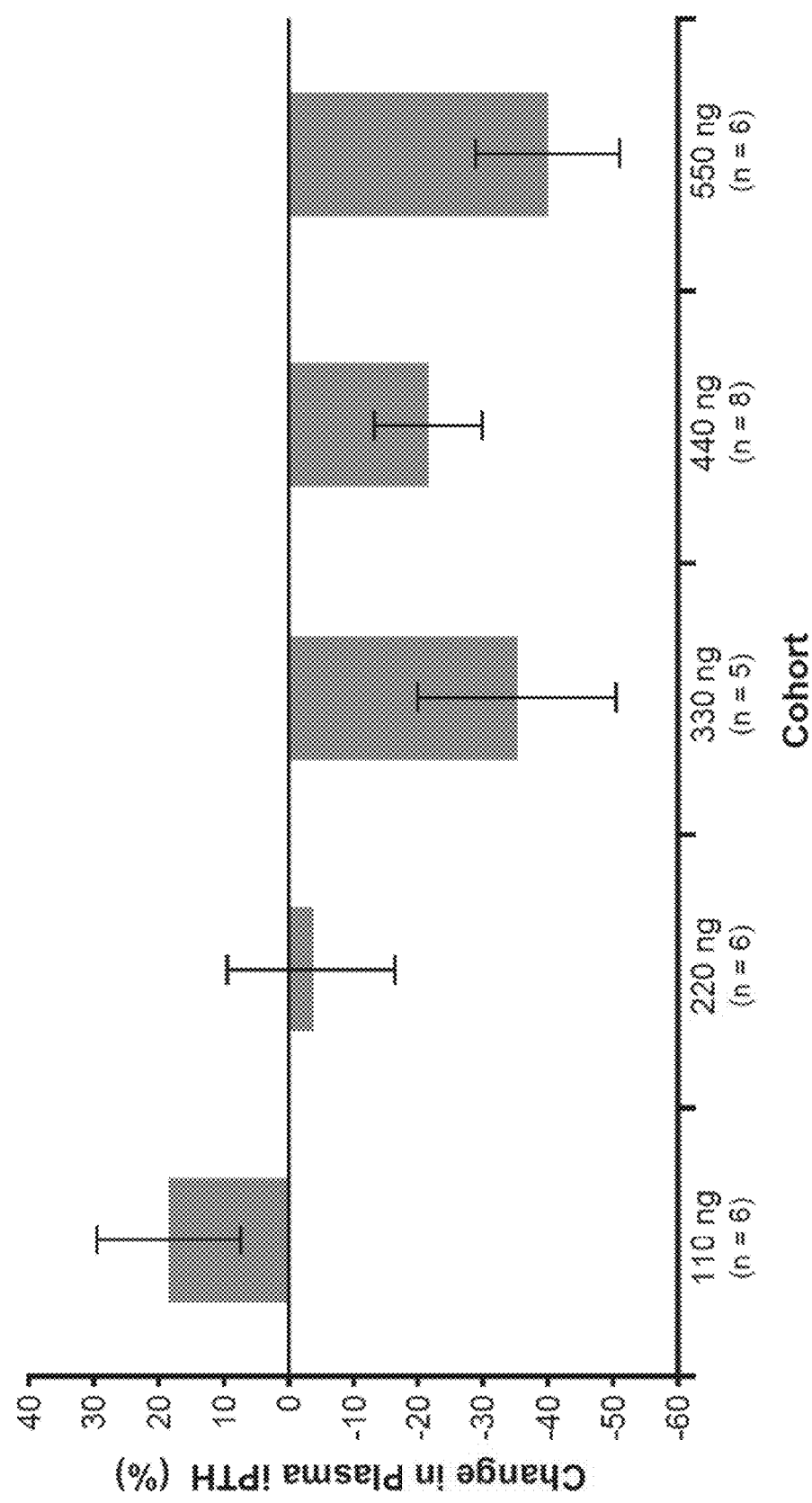
FIG. 1. Change in plasma iPTH (%) versus concentration of DP001 (2MD). Chronic kidney disease—stage 5 patients were given DP001 at the indicated dose orally 3 times weekly for 4 weeks. Data are presented as mean±SEM. Plasma iPTH levels were measured using the Immulite Intact iPTH Assay from Siemens Healthcare Diagnostics.

Disclosed are methods of treating and/or preventing secondary hyperparathyroidism or the symptoms thereof, including treating and/or preventing secondary hyperparathyroidism and/or the symptoms thereof in a subject previously treated with a calcimimetic. The disclosed methods further may described as follows based on the following definitions.

As used in this specification and the claims, the singular forms "a," "an," and "the" include plural forms unless the content clearly dictates otherwise. For example, "an active vitamin D compound" or "AVD," should be interpreted to mean "one or more AVDs," and "a calcimimetic" or "CM" should be interpreted to mean "one or more CMs."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

As used herein, the term "patient," which may be used interchangeably with the terms "subject" or "individual," refers to one who receives medical care, attention or treatment and may encompass a human patient. The disclosed methods may be utilized to treat and/or prevent secondary hyperthyroidism of the symptoms thereof in a patient in need thereof, including a patient previously treated with a calcimimetic. A patient in need thereof may include, but is not limited to, a patient having or at risk for developing secondary hyperthyroidism subsequent to a renal disease or disorder, including a patient previously treated with a calcimimetic. A patient in need thereof may include, but is not limited to, a patient having or at risk for developing secondary hyperthyroidism subsequent to renal osteodystrophy, for example, due to renal failure, including a patient previously treated with a calcimimetic. A patient in need thereof may include a patient undergoing renal dialysis, including a patient previously treated with a calcimimetic. A patient in need thereof may include, but is not limited to, a patient having or at risk for developing secondary hyperthyroidism as a result of a gastrointestinal malabsorption syndromes (e.g., chronic pancreatitis, small bowel disease, and malabsorption-dependent bariatric surgery in which the intestines do not absorb vitamins and minerals properly), including a patient previously treated with a calcimimetic. A patient in need thereof may include, but is not limited to, a patient having or at risk for developing secondary hyperthyroidism as a result of a long-term lithium therapy, vitamin D deficiency, malnutrition, vitamin D-resistant rickets, or hypermagnesemia (i.e., abnormally high blood magnesium levels), including a patient previously treated with a calcimimetic.

The disclosed methods may be utilized to treat and/or prevent the symptoms of secondary hyperthyroidism in a patient in need thereof, including a patient previously treated with a calcimimetic. Symptoms of secondary hyperthyroidism treated and/or prevented by the disclosed methods may include, but are not limited to: increased levels of serum PTH, serum phosphorus, and serum creatinine. Other symptoms of secondary hyperthyroidism treated and/or prevented by the disclosed methods may include: weakening of the bones; calciphylaxis (when calcium forms clumps in the skin and lead to ulcers and potentially death of surrounding tissue); cardiovascular complications; abnormal fat and sugar metabolism; itching (pruritis); and low blood counts (anemia). Further symptoms of secondary hyperthyroidism treated and/or prevented by the disclosed methods may include: bone and joint pain, bone deformities, broken bones (fractures), swollen joints, kidney stones, increased urination, muscle weakness and pain, nausea, and loss of appetite. Even further symptoms of secondary hyperthyroidism treated and/or prevented by the disclosed methods may include: fatigue, upper abdominal pain, and depression.

Previously, it has been demonstrated that calcitriol administered through the diet can effectively prevent renal disease and renal failure by reducing the symptoms of renal disease. (See James Wonkee Kim. Effects of calcitriol on the MRL/MpJ-fas/lpr model of systemic lupus erythematosus (Ph.D. Thesis, University of Wisconsin-Madison (2009)). For instance, it has been previously shown that administering calcitriol completely prevents proteinuria in the MRL/MpJ-FAS$^{lpr}$ (MRL/lpr) mouse model of systemic lupus erythematosus (SLE). (See id.). However, severe hypercalcemia always accompanied this treatment. Hypercalcemia (i.e., increased levels of calcium in the blood) can result in serious physical problems, including death. Specifically, an increase in calcium of approximately 2 mg/100 ml is considered mild hypercalcemia and is not considered a problem. However, an increase in calcium levels of more than 2 mg/100 ml is considered severe hypercalcemia and can cause calcification of the kidney, heart, and aorta. Clearly, the use of this compound is not optimal to treat or prevent secondary hyperparathyroidism, or the symptoms thereof, because of the resultant hypercalcemia.

2-methylene-19-nor-(20S)-1α,25-dihydroxyvitamin $D_3$ (2MD) is an analog of 1,25(OH)$_2$D$_3$ which has been shown to have increased in vivo potency toward bone but not on intestinal calcium absorption. The overall synthesis of 2MD is illustrated and described more completely in U.S. Pat. No. 5,843,928, issued Dec. 1, 1998, and entitled "2-Alkylidene-19-Nor-Vitamin D Compounds" the specification of which is specifically incorporated herein by reference. The biological activity of 2MD is also reported in U.S. Pat. No. 5,843,928 and in Shevde et al., "A Potent Analog of 1α,25-dihydroxyvitamin D$_3$ Selectively Induces Bone Formation" PNAS, Vol. 99, No. 21 pp 13487-13491 (2002), both of which are specifically incorporated herein by reference.

Surprisingly, in the methods disclosed herein, 2MD can be administered to treat and/or prevent secondary hyperparathyroidism and/or its accompanying symptoms preferably without causing severe hypercalcemia in a patient in need thereof, including a patient previously treated with a calcimimetic. As used herein, "hypercalcemia" means elevated calcium levels in the blood. In a normal subject, calcium levels are approximately 9-10.5 mg/dL or 2.2-2.6 mmol/L. As such, calcium levels greater than about 10.5 mg/dL or 2.6 mmol/L may be indicative of hypercalcemia. In cases of severe hypercalcemia (i.e., calcium levels above 15-16 mg/dL or 3.75-4 mmol/L) coma and cardiac arrest can develop. In the methods disclosed herein, 2MD can be administered to treat and/or prevent secondary hyperparathyroidism and/or its accompanying symptoms including elevated PTH levels, elevated phosphorus levels, and elevated creatinine levels.

Also in the methods disclosed herein, 2MD can be used to treat and reduce the severity of secondary hyperparathyroidism of renal disease and its accompanying symptoms in a patient in need thereof, including a patient previously treated with a calcimimetic, preferably without causing severe hypercalcemia, by reducing PTH, phosphorus, and creatinine levels in blood.

The present invention therefore provides novel methods of treating and/or preventing secondary hyperparathyroidism and/or its accompanying symptoms in a subject at risk of developing secondary hyperparathyroidism, and of treating and/or preventing secondary hyperparathyroidism and/or its accompanying symptoms in a subject exhibiting symptoms of secondary hyperparathyroidism, by administering to the subject a therapeutically effective amount of 2-methylene-19-nor-(20S)-1α,25-dihydroxyvitamin $D_3$ (2MD) or pharmaceutically acceptable salts thereof preferably without inducing hypercalcemia in the subject, where 2MD has the structure (I):

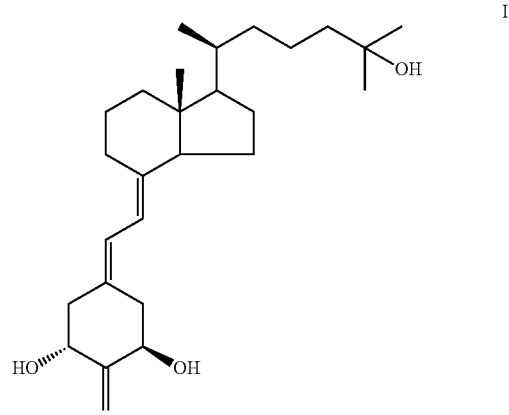 [SMILES: C=C1[C@H](O)CC(=C/C=C2\CCC[C@@]3(C)C2CCC3[C@@H](C)CCCC(C)(C)O)C[C@H]1O]

I

The disclosed methods may include administering 2MD to a patient that previously was administered a calcimimetic (e.g., in order to treat and/or prevent secondary hyperparathyroidism and/or the symptoms thereof). In some embodiments of the disclosed methods, after 2MD is administered to the patient, administration of the calcimimetic is discontinued. In other embodiments of the disclosed methods, the patient is administered 2MD and a calcimimetic (e.g., in order to treat and/or prevent secondary hyperparathyroidism and/or the symptoms thereof). For example, 2MD may be administered to the patient before, concurrently, or after the calcimimetic is administered to the patient.

As utilized herein, a calcimimetic is an agent that mimics the effect of calcium on the parathyroid gland. As such, calcimimetics increase the sensitivity of the calcium-sensing receptor (CaR) to circulating serum calcium, reducing the secretion of PTH and the serum calcium concentration. Calcimimetics may include, but are not limited to the compound named (R)—N-[1-(1-naphthyl)ethyl]-3-[3-(trifluoromethyl)phenyl]propan-1-amine otherwise referred to as "cinacalcet."

As used herein, "preventing" means forestalling of a clinical symptom indicative of secondary hyperparathyroidism. Such forestalling includes, for example, the maintenance of normal kidney functions in a subject at risk of developing secondary hyperparathyroidism prior to the development of overt symptoms of secondary hyperparathyroidism including, but not limited to, increased levels of serum PTH, phosphorus and creatinine. Therefore, the term "preventing" includes the prophylactic treatment of subjects to guard them from the occurrence of secondary hyperparathyroidism. Preventing secondary hyperparathyroidism in a subject is also intended to include inhibiting or arresting the development of secondary hyperparathyroidism. Inhibiting or arresting the development of secondary hyperparathyroidism includes, for example, inhibiting or arresting the occurrence of increased levels of serum PTH, phosphorus and creatinine.

As used herein, a "renal disease" or a "renal disorder" means a condition exhibiting impaired kidney function in a subject who is not on dialysis or a patient with chronic kidney disease (CKD) at stages 2 or 3, such as, for instance, acute kidney failure, acute nephritic syndrome, analgesic nephropathy, atheroembloic renal disease, chronic kidney failure, chronic nephritis, congenital nephrotic syndrome, goodpasture syndrome, interstitial nephritis, kidney cancer, kidney damage, kidney infection, kidney injury, kidney stones, membranoproliferative GNI, membranoproliferative GNII, membranous nephropathy, minimal change disease, necrotizing glomerulonephritis, nephroblastoma, nephrocalcinosis, nephrogenic diabetes insipidus, nephropathy-IgA, nephrosis nephrotic syndrome, polycystic kidney disease, post-strepococcal GN, reflux nephropathy, renal artery embolism, renal artery stenosis, renal disorders, renal papillary necrosis, renal tubular acidosis type I, renal tubular acidosis type II, renal underperfusion, renal vein thrombosis.

"Renal disease" is meant to include patients with established kidney failure (e.g., a glomerular filtration rate (GFR) of less than 15 mL/min/1.73 $m^2$ or permanent renal replacement therapy (RRT)). A subject having "renal disease" is meant to include a subject who has had kidney damage for more than 3 months, as defined by structural or functional abnormalities of the kidney, with or without decreased GFR, manifested by either pathological abnormalities or markers of kidney damage, including abnormalities in the composition of the blood or urine, or abnormalities in imaging tests. Markers of kidney damage include proteinuria of greater than 300 μg/day as measured by 24-HR excretion method. (See Table 15, Am. J. of Kidney Diseases, v. 39, no. 2, Suppl. 1 (February 2002), pp. 546-575, incorporated herein by reference). This definition may include patients on dialysis.

As used herein, a patient having "stage 2 chronic kidney disease (CKD)" means a patient exhibiting a mild reduction in GFR (60-89 mL/min/1.73 $m^2$). Kidney damage is defined as pathologic abnormalities or markers of damage, including abnormalities in blood or urine test or imaging studies. A patient having "stage 3 chronic kidney disease (CKD)" means a patient exhibiting a moderate reduction in GFR (30-59 mL/min/1.73 $m^2$). Guidelines for characterizing kidney disease may distinguish between stage 3A (GFR 45-59) and stage 3B (GFR 30-44) for purposes of screening and referral. For more information about stages of kidney disease, see Am. J. of Kidney Disease, V. 39, No. 2, Suppl. 1, February 2002, incorporated herein by reference. "Renal failure" is evidenced by a decreased glomeruli filtration rate (GFR) from a high value of 110 ml/minute/1.73 $m^2$ to 30 ml/minute/1.73 $m^2$ where dialysis is often initiated, and may be referred to as Stage 5, Chronic Kidney Disease (CKD).

As used herein, "administering" mean introducing a compound into the body, preferably into the systemic circulation, as described in more detail below. Examples include but are not limited to oral, topical, buccal, sublingual, pulmonary, transdermal, transmucosal, as well as subcutaneous, intraperitoneal, intravenous, and intramuscular injection or in the form of liquid or solid doses via the alimentary canal.

As used herein, "therapeutically effective" means an amount of a compound that, when administered to a subject for treating or preventing a disease, is sufficient to effect such treatment of prevention of the disease. A "therapeutically effective amount" will vary depending on the compound, the disease state being treated, the severity or the disease treated, the age and relative health of the subject, the route and form of administration, the judgment of the attending medical or veterinary practitioner, and other factors.

Pharmaceutical compositions for use in the disclosed treatment and prevention methods comprise an effective dose of 2MD as an active ingredient and a suitable carrier. An effective dose of 2MD for use in accordance with the disclosed methods is high enough for achieving a desired therapeutic effect and low enough so as not as to cause an undesired side effect (e.g., hypercalcemia). In some embodiments, pharmaceutical composition may comprise 2MD in a minimal dose of at least about 0.01, 0.05, 0.1, 0.5, 1.0, 5.0, 10.0, 50.0, 100.0, 500.0 or 1000.0 μg/gm of the composition. In other embodiments, pharmaceutical composition may comprise 2MD in a maximal dose no greater than 1000.0, 500.0, 100.0, 50.0, 10.0, 5.0, 1.0, 0.1, 0.05 μg/gm of the composition. The compositions may comprise 2MD within dose ranges having as end-points any of these disclosed doses (e.g., 0.01-1000.0 μg/gm of the composition). Minimal and/or maximal doses may be administered at any suitable frequency, such as daily, three times per week, weekly, or other frequencies.

In the disclosed treatment and prevention methods, a patient in need thereof may be administered an effective dose level of 2MD. An effective dose level of 2MD for use in accordance with the disclosed methods is high enough for achieving a desired therapeutic effect and low enough so as not as to cause an undesired side effect (e.g., hypercalcemia). In some embodiments, a minimal dose level for achieving therapy may be at least about 0.1, 0.25, 0.5, 1.0, 2.5, 5.0, 10.0, 12.5, 15.0, or 20.0 ng/kg body weight of the subject. In some embodiments, a maximal dose level may not exceed about 20.0, 15.0, 12.5, 10.0, 5.0, 2.5, 1.0, 0.5, 0.25, and 0.1 ng/kg body weight of the subject. Minimal and/or maximal dose levels may include dose level ranges having as end-points any of these discloses dose levels (e.g., 0.1-20.0 ng/kg body weight of the subject).

As used herein, "treat," "treating" or "treatment" means amelioration, alleviation or ablation of a clinical symptom indicative of secondary hyperparathyroidism. Amelioration, alleviation or ablation of a clinical symptom includes, for example, arresting, reducing the severity of or slowing the progression of or causing the regression of a symptom of secondary hyperparathyroidism. For instance, lowering the amount of serum PTH, serum phosphorus or serum creatinine levels in response to treatment with 2MD. Specifically, treating may include reducing the amount of serum PTH, serum phosphorus or serum creatinine pre-treatment versus post-treatment by at least about 20%, 30%, 40%, 50%, 60%, 70%, 80%, 90% or more. Other pathological conditions, chronic complications or phenotypic manifestations of secondary hyperparathyroidism are known to those skilled in the art and can similarly be used as a measure of treating secondary hyperparathyroidism so long as there is a reduction in the severity of the condition, complication or manifestation associated with the disease.

Effective compound formulations of 2MD are described in U.S. Pat. No. 5,843,928 and include pharmaceutical applications as a solution in innocuous solvents, or as an emulsion, suspension or dispersion in suitable solvents or carriers, or as pills, tablets, capsules combined with solid carriers. Other formulations may also include other pharmaceutically acceptable and nontoxic excipients such as stabilizers, anti-oxidants, binders, coloring agents or emulsifying or taste-modifying agents and extended release formulations.

In one embodiment, 2MD is the active pharmaceutical ingredient (API) administered in the disclosed methods. The API may be formulated in an oral pharmaceutical dosage form as a solution in innocuous solvents, emulsion, suspension or dispersion in suitable solvents or carriers. The API may also be formulated in various oral dosage forms, such as pills, tablets or capsules using suitable pharmaceutical solid carriers. Such pharmaceutical formulations may also contain other pharmaceutically suitable USP-approved inactive ingredients, excipients, such as stabilizers, anti-oxidants, binders, coloring agents, emulsifiers, and/or taste-modifying agents, which are referred to as USP approved inactive pharmaceutical ingredients.

The API may be administered orally, topically, parenterally or transdermally or by inhalation. The compound may be administered by injection or intravenous infusion using suitable sterile solutions. Topical dosage forms may be creams, ointments, patches, or similar vehicles suitable for transdermal and topical dosage forms. Preferably for the treatment of secondary hyperparathyroidism, or for the treatment or prevention of the symptoms of secondary hyperparathyroidism, the compound 2MD is administered either orally or parenterally (i.v.). The dose may be properly selected in accordance with the specific route of administration. In some embodiments, the patient may be administered a dose as low as 55 ng, 110 ng, 220 ng, 330 ng, 440 ng, 550 ng, or 660 ng, daily or 3 times per week in order to treat secondary hyperparathyroidism and/or to treat or prevent the symptoms thereof in a patient. In some embodiments, the patient may be administered a dose as high as 110 ng, 220 ng, 330 ng, 440 ng, 550 ng, 660 ng, or 770 ng, daily or 3 times per week in order to treat secondary hyperparathyroidism and/or to treat or prevent the symptoms thereof in a patient. Minimal and/or maximal doses may include dose ranges having as end-points any of these disclosed doses (e.g., 55 ng-770 ng).

The pharmaceutically suitable oral carrier systems (also referred to as drug delivery systems, which are modern technology, distributed with or as a part of a drug product that allows for the uniform release or targeting or drugs to the body) preferably include FDA-approved and/or USP-approved inactive ingredients. Under 21 CFR 210.3(b)(8), an inactive ingredient is any component of a drug product intended to furnish pharmaceutical activity or other direct effect in the diagnosis, or to affect the structure or any function of the body of humans or other animal. Active ingredients include those components of the product that may undergo chemical change during the manufacture of the drug product and be present in the drug product in a modified form intended to furnish the specified activity or effect. As used herein, a kit (also referred to as a dosage form) is a packaged collection of related material.

As used herein, "oral dosage" forms may include capsules (i.e., a solid oral dosage form consisting of a shell and a filling), whereby the shell is composed of a single sealed enclosure, or two halves that fit together and which are sometimes sealed with a band, and whereby capsule shells may be made from gelatin, starch, or cellulose, or other suitable materials, may be soft or hard, and are filled with a solid or liquid ingredients that can be poured or squeezed. The oral dosage form may also be a capsule or coated pellets, in which the drug is enclosed within either a hard or soft soluble container or "shell" made from a suitable form of gelatin. The drug itself may be in the form of granules to which varying amount of coating have been applied or in a capsule coated extended release, in which the drug is enclosed within either a hard or soft soluble container or "shell" made from a suitable form of gelatin. Additionally, the capsule may be covered in a designated coating which releases a drug or drugs in such a manner to allow at least a reduction in dosing frequency as compared to that drug or drugs presented as a conventional dosage form.

The oral dosage form may further be a capsule delayed release, in which the drug is enclosed within either a hard or soft soluble container made from a suitable form of gelatin, and which releases a drug (or drugs) at a time other than promptly after administration, whereby enteric-coated articles are delayed release dosage forms. Capsule delayed release pellets, in which the drug is enclosed within either a hard or soft container or "shell" are also useful. In these cases, the drug itself is in the form of granules to which enteric coating has been applied, thus delaying release of the drug until its passing into the intestine. Capsule extended release and capsule film-coated extended release are also useful.

Additionally, the capsule is covered in a designated film coating, and which releases a drug or drugs in such a manner to allow at least a reduction in dosing frequency as compared to that drug or drugs presented as a conventional dosage form), capsule gelatin coated (a solid dosage form in which the drug is enclosed within either a hard or soft soluble container made from a suitable form of gelatin; through a banding process, the capsule is coated with additional layers of gelatin so as to form a complete seal), capsule liquid filled (a solid dosage form in which the drug is enclosed within a soluble, gelatin shell which is plasticized by the addition of a polyol, such as sorbitol or glycerin, and is therefore of a somewhat thicker consistency than that of a hard shell capsule).

Typically, the active ingredients may be dissolved or suspended in a liquid vehicle, a granule (a small particle or grain), a pellet (a small sterile solid mass consisting of a highly purified drug, with or without excipients, made by the formation of granules, or by compression and molding), or a pellet coated extended release (a solid dosage form in which the drug itself is in the form of granules to which varying amounts of coating have been applied, and which releases a drug or drugs in such a manner to allow a reduction in dosing frequency as compared to that drug or drugs presented as a conventional dosage form).

Other forms include pills (a small, round solid dosage form containing a medicinal agent intended for oral administration), powder (an intimate mixture of dry, finely divided drugs and/or chemicals that may be intended for internal or external use), elixir (a clear, pleasantly flavored, sweetened hydroalcoholic liquid containing dissolved medicinal agents; it is intended for oral use), chewing gum (a sweetened and flavored insoluble plastic material of various shapes which when chewed, releases a drug substance into the oral cavity), syrup (an oral solution containing high concentrations of sucrose or other sugars; the term has also been used to include any other liquid dosage form prepared in a sweet and viscid vehicle, including oral suspensions), tablet (a solid dosage form containing medicinal substances with or without suitable diluents), tablet chewable (a solid dosage form containing medicinal substances with or without suitable diluents that is intended to be chewed, producing a pleasant tasting residue in the oral cavity that is easily swallowed and does not leave a bitter or unpleasant aftertaste), tablet coated or tablet delayed release, tablet dispersible, tablet effervescent, tablet extended release, tablet film coated, or tablet film coated extended release where the tablet is formulated in such manner as to make the contained medicament available over an extended period of time following ingestion.

In other forms, a tablet for solution, tablet for suspension, tablet multilayer, tablet multilayer extended release may be provided, where the tablet is formulated in such manner as to allow at least a reduction in dosing frequency as compared to that drug presented as a conventional dosage form. A tablet orally disintegrating, tablet orally disintegrating delayed release, tablet soluble, tablet sugar coated, osmotic, and the like are also suitable.

The oral dosage form composition may contain an active pharmaceutical ingredient and one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (e.g., anionic, cationic, amphoteric and nonionic), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

As used herein, the injectable and infusion dosage forms include, but are not limited to, a liposomal injectable, which either consists of or forms liposomes (a lipid bilayer vesicle usually composed of phospholipids which is used to encapsulate an active drug substance). An injection, which includes a sterile preparation intended for parenteral use; five distinct classes of injections exist as defined by the USP, is also suitable. An emulsion injection, which includes an emulsion consisting of a sterile, pyrogen-free preparation intended to be administered parenterally or a lipid complex injection are also suitable.

Other forms include a powder for solution injection, which is a sterile preparation intended for reconstitution to form a solution for parenteral use; a powder for suspension injection that is a sterile preparation intended for reconstitution to form a suspension for parenteral use; a powder lyophilized for liposomal suspension injection, which is a sterile freeze dried preparation intended for reconstitution for parenteral use which has been formulated in a manner that would allow liposomes (a lipid bilayer vesicle usually composed of phospholipids which is used to encapsulate an active drug substance, either within a lipid bilayer or in an aqueous space) to be formed upon reconstitution; a powder lyophilized for solution injection, which is a dosage form intended for the solution prepared by lyophilization ("freeze drying"), a process which involves the removal of water from products in the frozen state at extremely low pressures.

This is intended for subsequent addition of liquid to create a solution that conforms in all respects to the requirements for injections; a powder lyophilized for suspension injection being a liquid preparation, intended for parenteral use that contains solids suspended in a suitable fluid medium and conforms in all respects to the requirements for Sterile Suspensions; the medicinal agents intended for the suspension are prepared by lyophilization ("freeze drying"), a process which involves the removal of water from products in the frozen state at extremely low pressures; a solution injection being a liquid preparation containing one or more drug substances dissolved in a suitable solvent or mixture of mutually miscible solvents that is suitable for injection; a solution concentrate injection being a sterile preparation for parenteral use which, upon the addition of suitable solvents, yields a solution conforming in all respects to the requirements for injections.

A suspension injection comprises a liquid preparation, suitable for injection, which consists of solid particles dispersed throughout a liquid phase in which the particles are not soluble that can also consist of an oil phase dispersed throughout an aqueous phase, or vice-versa. A suspension liposomal injection comprises a liquid preparation, suitable for injection, which consists of an oil phase dispersed throughout an aqueous phase in such a manner that liposomes (a lipid bilayer vesicle usually composed of phospholipids which is used to encapsulate an active drug substance, either within a lipid bilayer or in an aqueous space) are formed. A suspension sonicated injection comprises a liquid preparation, suitable for injection, which consists of solid particles dispersed throughout a liquid phase in which the particles are not soluble. In addition, the product is sonicated while a gas is bubbled through the suspension, and this results in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives. Formulations suitable for parenteral administration conveniently comprise a sterile oily or aqueous preparation of the active ingredient which is preferably isotonic with the blood of the recipient.

As used herein, inhalation dosage forms include, but are not limited to, aerosol being a product that is packaged under pressure and contains therapeutically active ingredients that are released upon activation of an appropriate valve system intended for topical application to the skin as well as local application into the nose (nasal aerosols), mouth (lingual and sublingual aerosols), or lungs (inhalation aerosols); foam aerosol being a dosage form containing one or more active ingredients, surfactants, aqueous or nonaqueous liquids, and the propellants, whereby if the propellant is in the internal (discontinuous) phase (i.e., of the oil-in-water type), a stable foam is discharged, and if the propellant is in the external (continuous) phase (i.e., of the water-in-oil type), a spray or a quick-breaking foam is discharged; metered aerosol being a pressurized dosage form consisting of metered dose valves which allow for the delivery of a uniform quantity of spray upon each activation; powder aerosol being a product that is packaged under pressure and contains therapeutically active ingredients, in the form of a powder, that are released upon activation of an appropriate valve system; and, aerosol spray being an aerosol product which utilizes a compressed gas as the propellant to provide the force necessary to expel the product as a wet spray and being applicable to solutions of medicinal agents in aqueous solvents.

As used herein, transdermal dosage forms include, but are not limited to, a patch being a drug delivery system that often contains an adhesive backing that is usually applied to an external site on the body, whereby the ingredients either passively diffuse from, or are actively transported from, some portion of the patch, and whereby depending upon the patch, the ingredients are either delivered to the outer surface of the body or into the body; and, other various types of transdermal patches such as matrix, reservoir and others known in the art.

As used herein, topical dosage forms include various dosage forms known in the art such as lotions (an emulsion, liquid dosage form, whereby this dosage form is generally for external application to the skin), lotion augmented (a lotion dosage form that enhances drug delivery, whereby augmentation does not refer to the strength of the drug in the dosage form), gels (a semisolid dosage form that contains a gelling agent to provide stiffness to a solution or a colloidal dispersion, whereby the gel may contain suspended particles) and ointments (a semisolid dosage form, usually containing less than 20% water and volatiles and greater than 50% hydrocarbons, waxes, or polyols as the vehicle, whereby this dosage form is generally for external application to the skin or mucous membranes).

Ointment augmented (an ointment dosage form that enhances drug delivery, whereby augmentation does not refer to the strength of the drug in the dosage form), creams (an emulsion, semisolid dosage form, usually containing greater than 20% water and volatiles and/or less than 50% hydrocarbons, waxes, or polyols may also be used as the vehicle, whereby this dosage form is generally for external application to the skin or mucous membranes. Cream augmented (a cream dosage form that enhances drug delivery, whereby augmentation does not refer to the strength of the drug in the dosage form), emulsions (a dosage form consisting of a two-phase system comprised of at least two immiscible liquids, one of which is dispersed as droplets, internal or dispersed phase, within the other liquid, external or continuous phase, generally stabilized with one or more emulsifying agents, whereby emulsion is used as a dosage form term unless a more specific term is applicable, e.g. cream, lotion, ointment), suspensions (a liquid dosage form that contains solid particles dispersed in a liquid vehicle), suspension extended release, pastes (a semisolid dosage form, containing a large proportion, 20-50%, of solids finely dispersed in a fatty vehicle, whereby this dosage form is generally for external application to the skin or mucous membranes), solutions (a clear, homogeneous liquid dosage form that contains one or more chemical substances dissolved in a solvent or mixture of mutually miscible solvents), and powders are also suitable.

Jellies (a class of gels, which are semisolid systems that consist of suspensions made up of either small inorganic particles or large organic molecules interpenetrated by a liquid—in which the structural coherent matrix contains a high portion of liquid, usually water) and films (a thin layer or coating), including film extended release (a drug delivery system in the form of a film that releases the drug over an extended period in such a way as to maintain constant drug levels in the blood or target tissue) and film soluble (a thin layer or coating which is susceptible to being dissolved when in contact with a liquid) are also suitable.

Patches (a drug delivery system that often contains an adhesive backing that is usually applied to an external site on the body, whereby its ingredients either passively diffuse from, or are actively transported from, some portion of the patch, whereby depending upon the patch, the ingredients are either delivered to the outer surface of the body or into the body, and whereby a patch is sometimes synonymous with the terms 'extended release film' and 'system'), patch extended release (a drug delivery system in the form of a patch that releases the drug in such a manner that a reduction in dosing frequency compared to that drug presented as a conventional dosage form, e.g., a solution or a prompt drug-releasing, conventional solid dosage form), patch extended release electronically controlled (a drug delivery system in the form of a patch which is controlled by an electric current that releases the drug in such a manner that a reduction in dosing frequency compared to that drug presented as a conventional dosage form, e.g., a solution or a prompt drug-releasing, conventional solid dosage form), and the like. The various topical dosage forms may also be formulated as immediate release, controlled release, sustained release, or the like.

The topical dosage form composition contains an active pharmaceutical ingredient and one or more inactive pharmaceutical ingredients such as excipients, colorants, pigments, additives, fillers, emollients, surfactants (e.g., anionic, cationic, amphoteric and nonionic), penetration enhancers (e.g., alcohols, fatty alcohols, fatty acids, fatty acid esters and polyols), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

EXAMPLES

The following examples are presented for illustrative purposes only, and are not intended to limit the scope of the present invention in any way. The examples illustrate that 2MD, an analog of $1,25(OH)_2D_3$ originally thought to be important in prevention and treatment of osteoporosis, is also important in preventing and treating secondary hyperparathyroidism and its accompanying symptoms in a patient in need thereof, including a patient previously treated with a calcimimetic.

Title: 2MD, A New Treatment for Secondary Hyperparathyroidism: A Phase 2B, Double-Blind, Randomized, Placebo-Controlled Study in Hemodialysis Patients Reference is made to "2MD, A New Treatment for Secondary Hyperparathyroidism: A Phase 2B, Double-Blind, Randomized, Placebo-Controlled Study in Hemodialysis Patients," Hector F. DeLuca, Julia B. Zella, Danielle C. Knutson, Lori A. Plum, and Margaret Clagett-Dame, Poster Presentation at the 2014 American Society of Nephrology, Kidney Week Meeting, November 2014.

Background

Secondary hyperparathyroidism (SHPT) has been successfully managed with the use of active vitamin D analogs (AVDs) alone, or with the addition of a calcimimetic (CM). However, both classes of compounds have drawbacks.

Hypercalcemia is of concern when AVDs are used, while CMs can cause hypocalcemia and have compliance issues because of nausea and vomiting. A novel, highly potent AVD (2-methylene-19-nor-(20S)-1α,25-dihydroxyvitamin D3, 2MD or DP001) specifically targets the parathyroid glands and bone and is being developed for the treatment of SHPT in patients on hemodialysis.

Study and Results

Dose Selection.

A Phase 2A, open-label, dose-ranging study of DP001 in hemodialysis patients was conducted to determine a starting dose of DP001 for the Phase 2B, randomized, placebo-controlled study described in this Example. Given orally 3 times weekly for 4 weeks, DP001 suppresses PTH in dialysis patients in a dose-dependent fashion without changing serum calcium. (See FIGS. 1 and 2). Based on the results in FIGS. 1 and 2, an efficacious and safe starting dose of 440 ng was chosen. Data are presented as mean±SEM. Plasma iPTH levels were measured using the Immulite Intact iPTH Assay from Siemens Healthcare Diagnostics.

Eligibility Criteria.

Subjects in the study met the following eligibility criteria: men and non-pregnant women≥18 years of age; exhibiting end stage renal disease (ESRD) or chronic kidney disease (CKD) stage 5 (GFR<15 mL/min/1.73 m$^2$)) and on hemodialysis 3×/week>3 months; prior active vitamin D use required; prior cinacalcet use allowed but not required; first screen: Ca≤10.5 mg/dL, P≤7.0 mg/dL, iPTH≤500 pg/mL; final screen: Ca≤9.8 mg/dL, P≤6.5 mg/dL, iPTH≥300 pg/mL; vitamin $D_2$ or $D_3$ limited to ≤4000 IU/day (or equivalent); P binders allowed but class must stay consistent; and no severe heart or liver problems, active malignancies or infections, calciphylaxis, or PTx.

Study.

Figure 3:
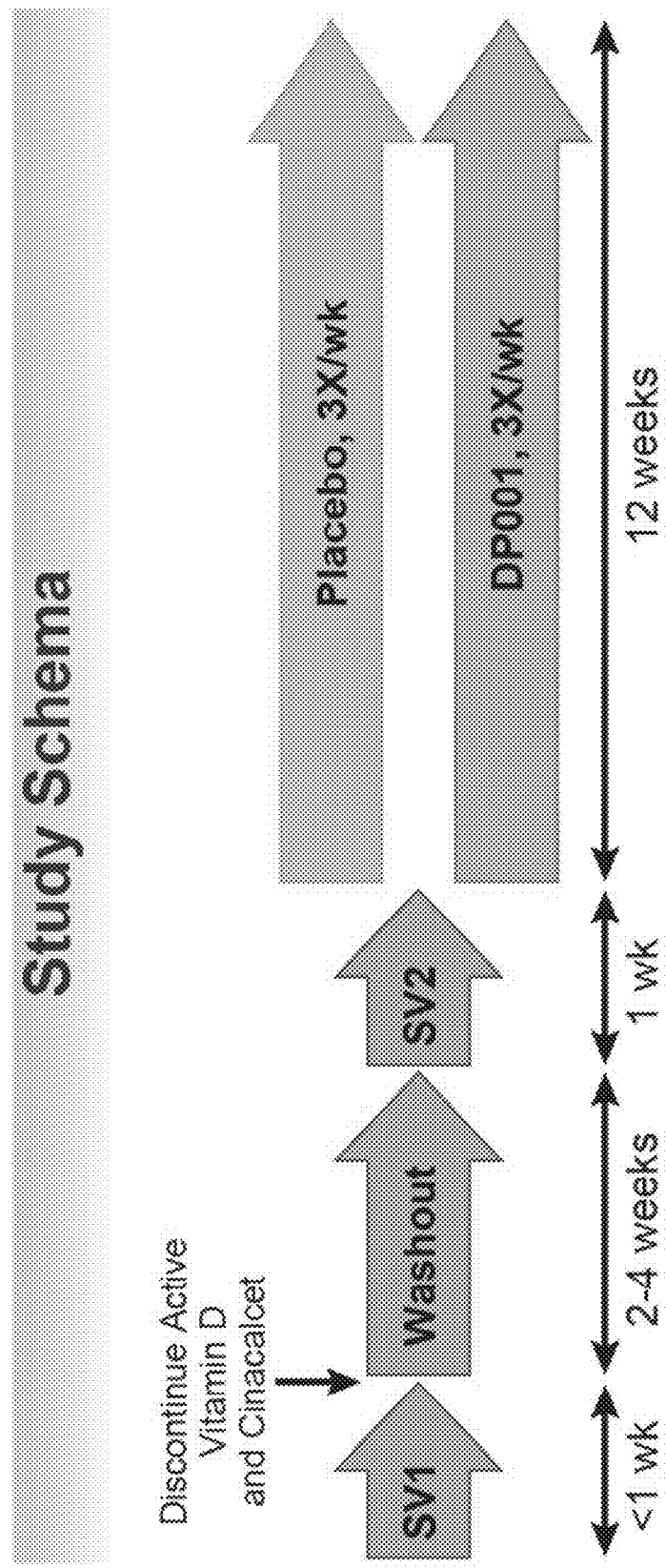
FIG. 3. Study schema for study participants. Participants discontinued use of the active vitamin D analogue (AVD) and cinacalcet (if applicable) prior to a washout period and subsequent administration of placebo or DP001 (440 ng, 3×/wk, for up to 12 weeks).
Figure 4:
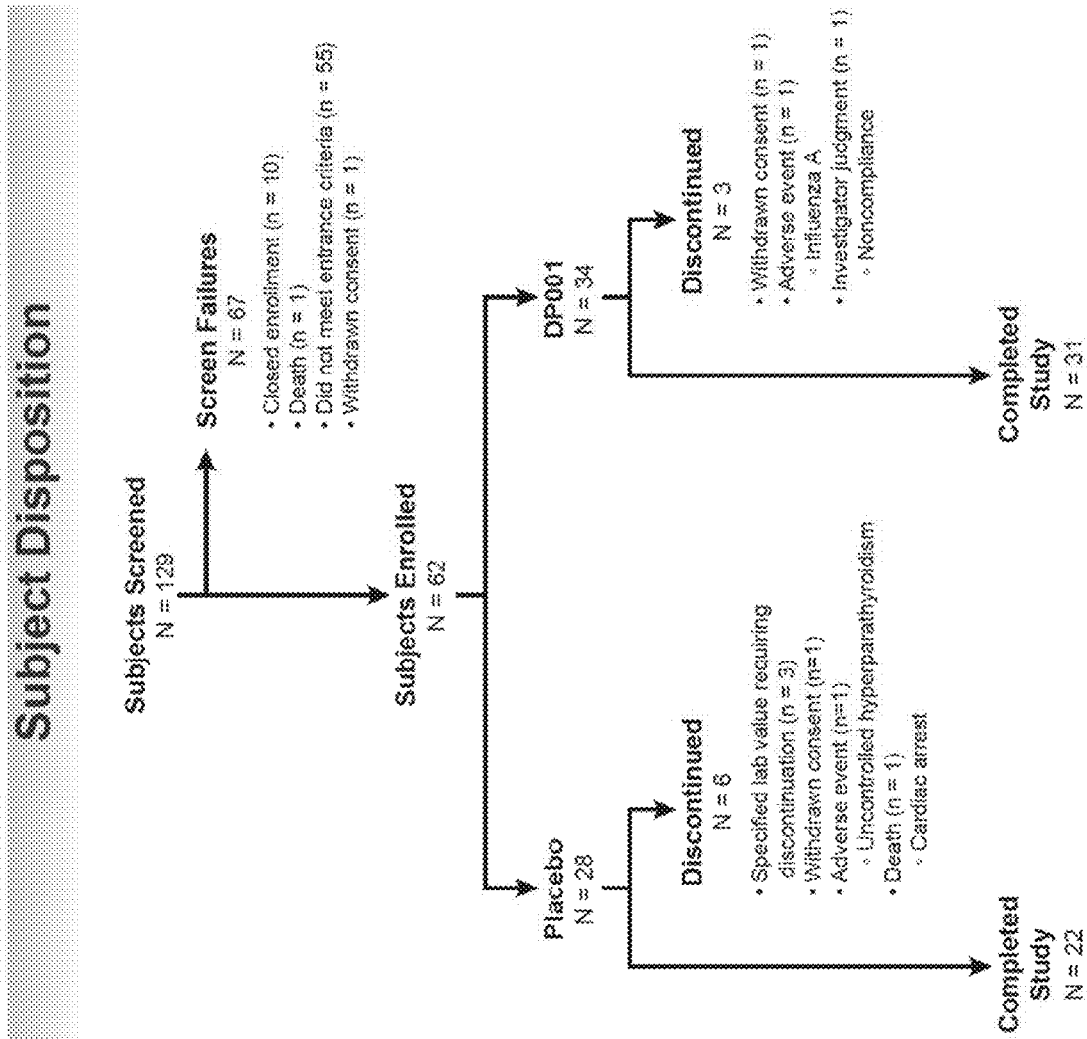
FIG. 4. Subject disposition tree.

Subjects were administered DP001 (2MD) or placebo accordingly the study schema of FIG. 3. Subject disposition is illustrated in FIG. 4. As indicated, 129 subject were screened. Of these, 62 were enrolled and 67 were screen failures. Of the 62 enrollees, 28 were administered a placebo and 34 were administered DP001 (440 ng, 3×/wk for up to 12 weeks). Of the 28 enrollees who were administered the placebo, 22 completed the 12 week study and 6 discontinued for reasons illustrated. Of the 34 enrollees who were administered DP001, 31 completed the 12 week study and 3 discontinued for reasons illustrated.

Demographics and Baseline Characteristics.

The demographics and baseline characteristics of the subjects enrolled in the study are presented in FIG. 5.

Primary Efficacy Endpoint.

Figure 6:
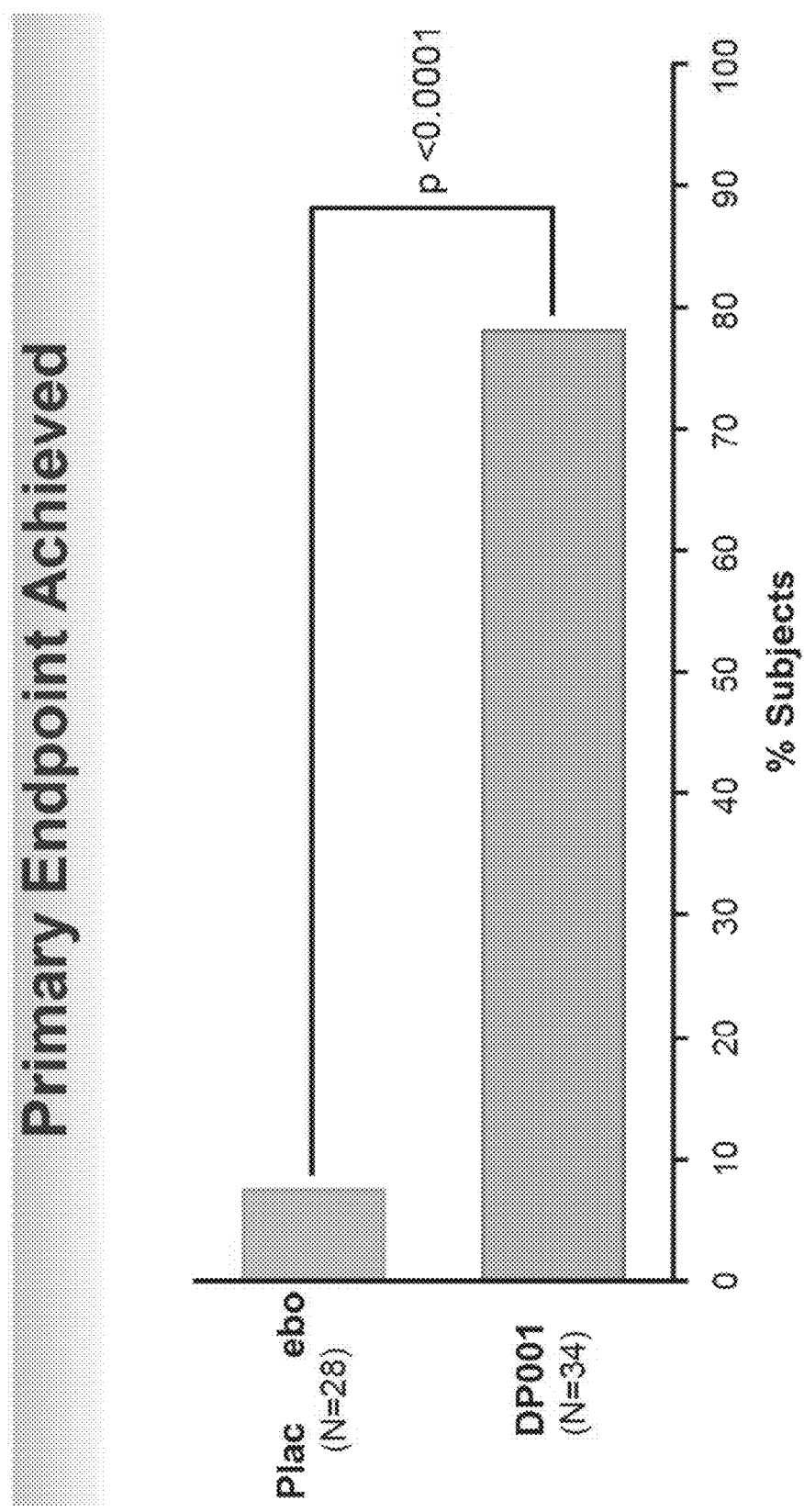
FIG. 6. Percentage of subjects achieving primary endpoint of two consecutive ≥30% decrease from his/her averaged baseline iPHT level during the 12-week treatment period. Pre-dialysis serum iPTH levels were measured using the Access Intact iPTH Assay from Beckman Coulter ($p<0.0001$, Fisher's exact test).

The Primary Efficacy Endpoint was the proportion of subjects who achieved two consecutive ≥30% decrease from his/her Averaged Baseline iPTH level during the 12-week treatment period. (See FIG. 6). Pre-dialysis serum iPTH levels were measured using the Access Intact iPTH Assay from Beckman Coulter (p<0.0001, Fisher's exact test).

Secondary Efficacy Endpoint.

Figure 7:
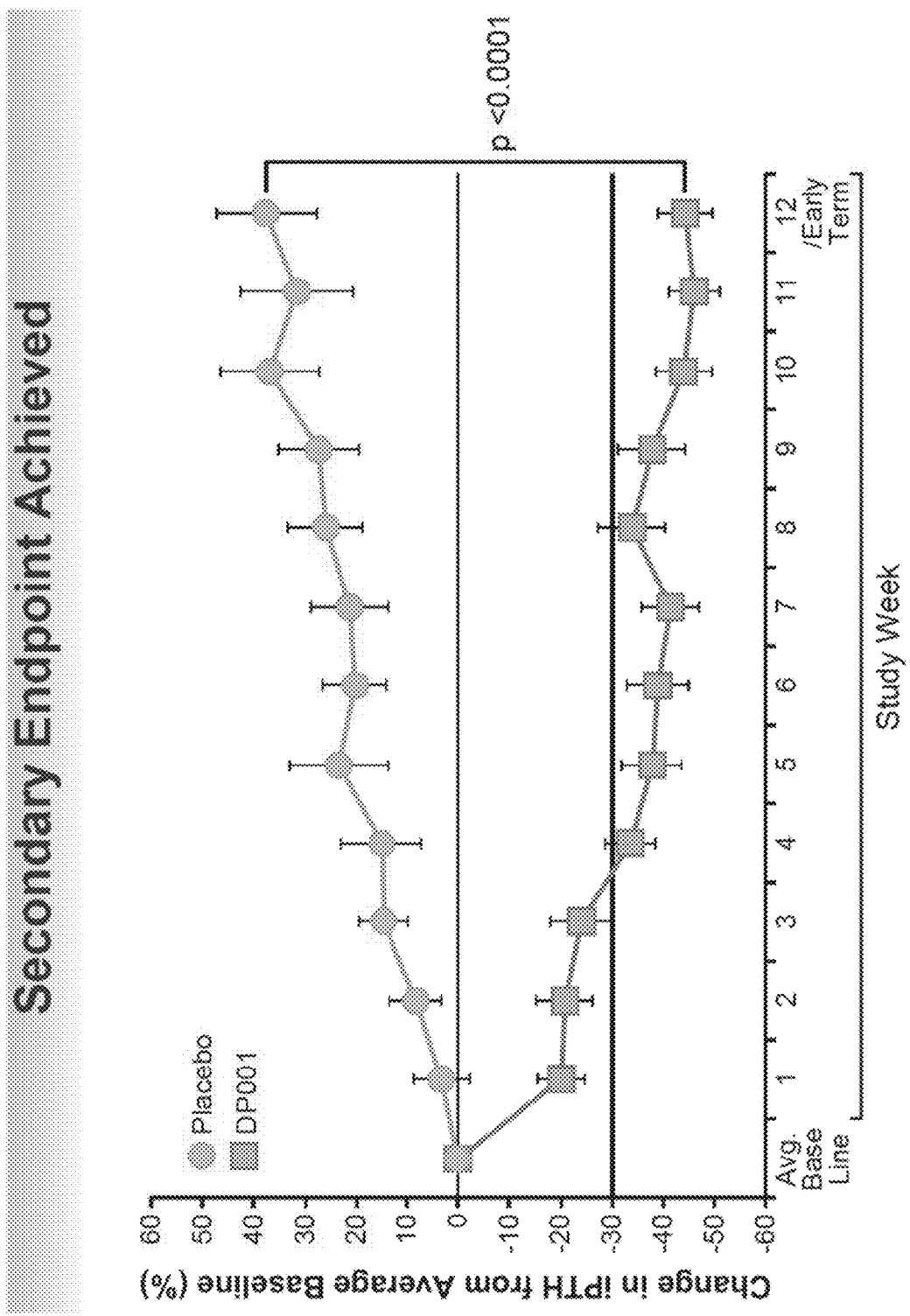
FIG. 7. Secondary efficacy endpoint as measured as the mean percentage change in serum iPTH from the averaged baseline value to the average of the last 2 on-treatment values. Data are presented as mean±SEM. $p<0.0001$, One-way ANOVA.

The secondary efficacy endpoint was the mean percentage change in serum iPTH from the Averaged Baseline value to the average of the last 2 on-treatment values. Data are presented in FIG. 7 as mean±SEM. p<0.0001, One-way ANOVA.

DP001 Alone Lowers iPTH in CKD-5D Patients Previously on Cinacalcet.

Figure 8:
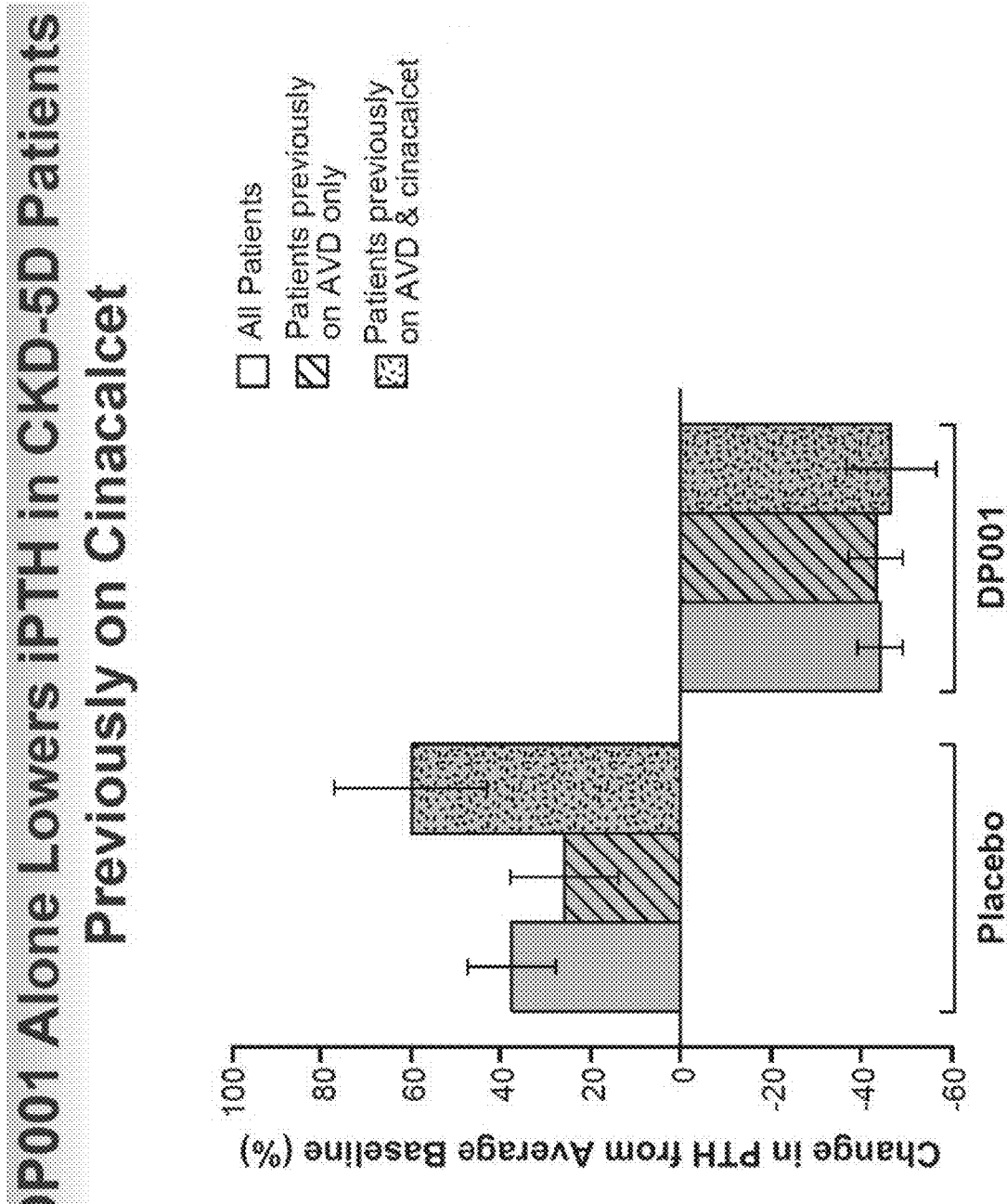
FIG. 8. Change in PTH from averaged baseline (%) for "All Patients," "Patients Previously on Active Vitamin D Analogue (AVD) only," and "Patients on AVD and Cinacalcet" administered placebo or DP001.

As illustrated in FIG. 8, DP001 (2MD) effectively reduced PTH levels in subject previously being treated with an active vitamin D analogue (AVD) and a calcimimetic (CM) in the form of cinacalcet.

Safety Results—Endpoints.

Safety results and endpoints are presented in FIG. 9. Of the 14 subjects that reached the safety threshold for PTH, 6 had been dose-adjusted downward following an upward adjustment, suggesting insufficient time was allotted for PTH levels to respond to DP001 (2MD). The remaining 8 subjects were only dose-adjusted downward, indicating a starting dose lower than 440 ng would have been sufficient to suppress PTH. The corrected-serum calcium and phosphorus product safety threshold was surpassed in two patients that also had high serum phosphorus values at baseline (7.8 mg/dL and 9.4 mg/dL), suggesting that phosphorus homeostasis was difficult to manage in these patients even before any exposure to DP001 (2MD). Only one patient receiving DP001 (2MD) had two consecutive corrected serum calcium values>10.5 mg/dL.

Safety Results—Adverse Events.

Safety results and adverse events (AEs) are presented in FIG. 10. No serious adverse events (SAEs) were judged by the investigators to be related to DP001.

SUMMARY AND CONCLUSIONS

A novel analog (2MD or DP001) of calcitriol that selectively targets the parathyroid gland is being developed for the treatment of secondary hyperparathyroidism (SHPT) in subjects having chronic kidney diseases stage 5 (CKD-5D). In the Phase 2B double-blind, placebo-controlled study, 3× weekly oral DP001 reduced serum iPTH by 46% in 78% of subjects by 12 weeks of treatment (p<0.0001), satisfying both primary and secondary endpoints. DP001 alone successfully treats SHPT in patients previously taking a calcimimetic. There were no significant differences in adverse event reporting between treatment groups. Serum calcium values remained in the normal range, and changes in serum phosphorus were similar between Placebo and DP001 groups.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue or prior invention.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method of treating secondary hyperparathyroidism or the symptoms thereof in a subject having secondary hyperparathyroidism or at risk for developing secondary hyperparathyroidism, the method comprising administering a therapeutically effective amount of 2-methylene-19-nor-(20S)-1α,25-dihydroxyvitamin $D_3$ (2MD) or a pharmaceutically acceptable salt thereof to the subject and concurrently administering a therapeutically effective amount of a calcimimetic to the subject wherein secondary hyperparathyroidism or the symptoms thereof are treated.

2. The method of claim 1, wherein secondary hyperparathyroidism is treated without inducing hypercalcemia in the subject.

3. The method of claim 1, wherein the subject is administered the therapeutically effective amount of 2MD three times per week.

4. The method of claim 1, wherein the 2MD is formulated in an oral, topical, transdermal, parenteral, injection or infusion dosage form.

5. The method of claim 1, wherein the symptoms of secondary hyperparathyroidism comprise elevated serum PTH.

6. The method of claim 1, wherein the symptoms of secondary hyperparathyroidism comprise elevated serum phosphorus.

7. The method of claim 1, wherein the symptoms of secondary hyperparathyroidism comprise elevated serum creatinine.

8. A method of treating secondary hyperparathyroidism or the symptoms thereof in a subject having secondary hyperparathyroidism or at risk for developing secondary hyperparathyroidism, wherein the subject has chronic kidney disease-stage 5 (CKD-5D) and is receiving hemodialysis treatment, the method comprising administering a therapeutically effective amount of 2-methylene-19-nor-(20S)-1α, 25-dihydroxyvitamin $D_3$ (2MD) or a pharmaceutically acceptable salt thereof to the subject and concurrently administering a therapeutically effective amount of a calcimimetic to the subject wherein secondary hyperparathyroidism or the symptoms thereof are treated.

9. The method of claim 8, wherein secondary hyperparathyroidism is treated without inducing hypercalcemia in the subject.

10. The method of claim 8, wherein the subject is administered the therapeutically effective amount of 2MD three times per week.

11. The method of claim 8, wherein the 2MD is formulated in an oral, topical, transdermal, parenteral, injection or infusion dosage form.

12. The method of claim 8, wherein the symptoms of secondary hyperparathyroidism comprise elevated serum PTH.

13. The method of claim 8, wherein the symptoms of secondary hyperparathyroidism comprise elevated serum phosphorus.

14. The method of claim 8, wherein the symptoms of secondary hyperparathyroidism comprise elevated serum creatinine.

15. A method of treating secondary hyperparathyroidism or the symptoms thereof in a subject having secondary hyperparathyroidism or at risk for developing secondary hyperparathyroidism, the method comprising administering a therapeutically effective amount of 2-methylene-19-nor-(20S)-1α,25-dihydroxyvitamin $D_3$ (2MD) or a pharmaceutically acceptable salt thereof to the subject, wherein the therapeutically effective amount of 2MD is less than about 1.0 ng/kg body weight, and concurrently administering a therapeutically effective amount of a calcimimetic to the subject wherein secondary hyperparathyroidism or the symptoms thereof are treated.

16. The method of claim 15, wherein secondary hyperparathyroidism is treated without inducing hypercalcemia in the subject.

17. The method of claim 15, wherein the 2MD is formulated in an oral, topical, transdermal, parenteral, injection or infusion dosage form.

18. The method of claim 15, wherein the subject has chronic kidney disease-stage 5 (CKD-5D) and is receiving hemodialysis treatment.

19. The method of claim 15, wherein the symptoms of secondary hyperparathyroidism comprise elevated serum PTH.

20. The method of claim 15, wherein the symptoms of secondary hyperparathyroidism comprise elevated serum phosphorus.

21. The method of claim 15, wherein the symptoms of secondary hyperparathyroidism comprise elevated serum creatinine.

* * * * *